United States Patent
Kim et al.

(10) Patent No.: US 6,911,004 B2
(45) Date of Patent: Jun. 28, 2005

(54) MICRO CAPSULE ROBOT

(75) Inventors: ByungKyu Kim, Seongbuk-Gu (KR);
Seunghak Lee, Yeongdeungpo-Gu (KR); Jae-Wook Ryu, Gangnam-Gu (KR); YoungHun Tak, Sokcho (KR); Tae-Song Kim, Mapo-Gu (KR); Jong-Oh Park, Seocho-Gu (KR)

(73) Assignee: Korea Institute of Science and Technology (KR)

( * ) Notice: Subject to any disclaimer, the term of this patent is extended or adjusted under 35 U.S.C. 154(b) by 13 days.

(21) Appl. No.: 10/633,834

(22) Filed: Aug. 4, 2003

(65) Prior Publication Data

US 2004/0030454 A1 Feb. 12, 2004

(30) Foreign Application Priority Data

Aug. 9, 2002 (KR) .................. 10-2002-0047097

(51) Int. Cl.⁷ ................................ A61B 1/00
(52) U.S. Cl. ................ 600/101; 600/109; 600/118; 600/160
(58) Field of Search .................. 600/101, 109, 600/118, 160, 178–179, 114, 115, 117; 348/65, 68, 74–76; 700/245; 901/1; 356/241.6

(56) References Cited

U.S. PATENT DOCUMENTS

| 5,595,565 | A | * | 1/1997 | Treat et al. | 600/114 |
| 5,662,587 | A | * | 9/1997 | Grundfest et al. | 600/114 |
| 6,162,171 | A | * | 12/2000 | Ng et al. | 600/141 |
| 6,719,684 | B2 | * | 4/2004 | Kim et al. | 600/101 |
| 6,824,508 | B2 | * | 11/2004 | Kim et al. | 600/101 |
| 2002/0042562 | A1 | * | 4/2002 | Meron et al. | 600/361 |

* cited by examiner

Primary Examiner—Linda C. M. Dvorak
Assistant Examiner—Michael P. Straightiff
(74) Attorney, Agent, or Firm—Ostrolenk, Faber, Gerb & Soffen, LLP (57) ABSTRACT

A micro capsule robot comprises a body unit; a body movement control unit, which is installed on an outer circumferential surface of the body unit, including a linear driving device, and wings which are unfolded from the outer circumferential surface of the body unit by operation of the linear driving device for delaying or stopping the movement of the body unit; and a controlling unit installed in the body unit for controlling the body movement delay unit.

19 Claims, 9 Drawing Sheets

MICRO CAPSULE ROBOT

BACKGROUND OF THE INVENTION

1. Field of the Invention

The present invention relates to a micro capsule robot, and particularly, to a movement control of a micro capsule robot in organs.

2. Description of the Background Art

An endoscope is used when a lesion of organs in human body is desired to be examined and treated without an operation. However, in case of a colonscopy, a patient may feel pain and unpleasant feeling. Because the colon is bent with large angle, and therefore, the pain and lesion decision are greatly affected by experience and skill of the doctor.

Recently, in order to solve the problems of the colonscopy, a virtual colonscopy and a DNA test have been developed. However, these methods are indirect because the doctor can not directly see an affected part to care for the part and can not perform a biopsy. Also, a capsule which can be swallowed is developed to transmit image information of the small intestine to an outside apparatus, and thereby the small intestine which can not be seen by the conventional endoscope can be diagnosed and a range of medical diagnosis can be extended.

The above micro capsule type endoscope transmits information obtained by a camera system built therein to the outside apparatus using a radio transmission module, and thereby, the test range can be extended toward the small intestine.

However, the micro capsule having the radio camera system is moved according to peristalsis of organs, and therefore, the doctor can not stop the movements of the micro capsule even in case that the doctor wishes to examine a certain location.

The conventional micro capsule for examining the organs includes the image information transmission system, however, does not include a function for stopping or movement control.

SUMMARY OF THE INVENTION

Therefore, an object of the present invention is to provide a micro capsule robot which is able to control movements of itself in an organ, by delaying or stopping.

To achieve the object of the present invention, there is provided a micro capsule robot comprising: a body unit; a body movement control unit including a linear driving device and wings which are unfolded from an outer circumferential surface of the body unit by operation of the linear driving unit to contact with an inner wall of an organ and to control the movement of the body unit, and installed on the outer circumferential surface of the body unit; and a controlling unit installed in the body unit for controlling the body movement control unit.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

A micro capsule robot according to the present invention will be described with reference to accompanying Figures as follows.

Figure 1:
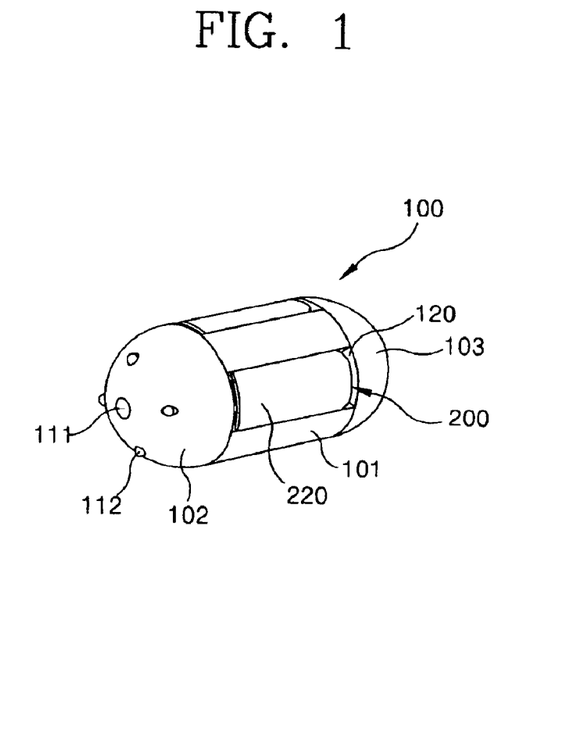
FIG. 1 is a perspective view showing a micro capsule robot according to the first embodiment of the present invention.
Figure 2:
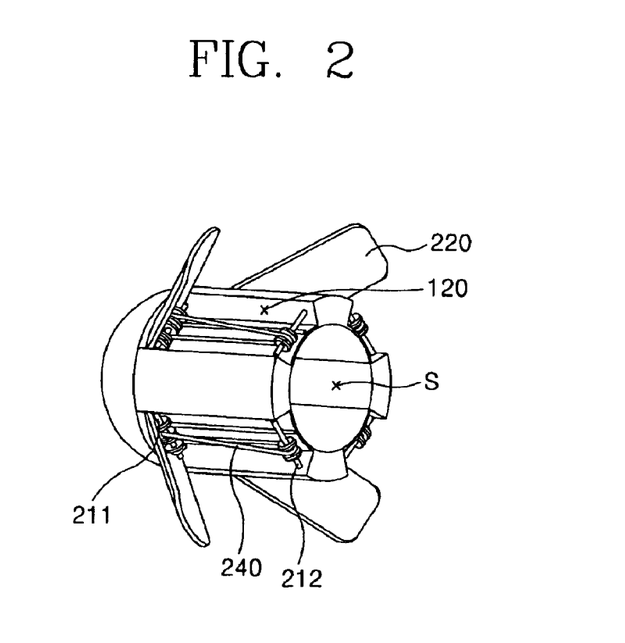
FIG. 2 is a perspective view showing a status that a wing of-the micro capsule robot shown in FIG. 1 is unfolded.
Figure 3:
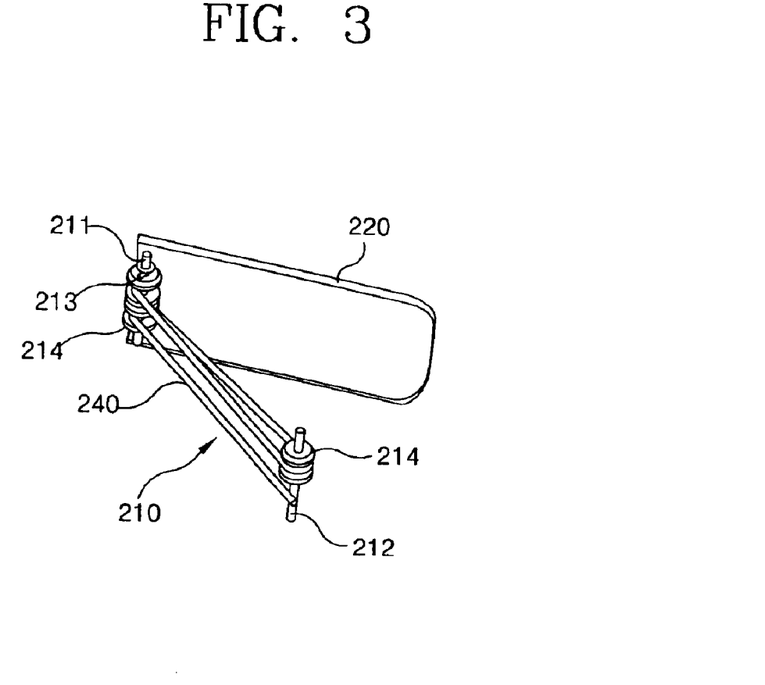
FIG. 3 is a perspective view showing driving principle of the wings in the micro capsule robot shown in FIG. 1.
Figure 4:
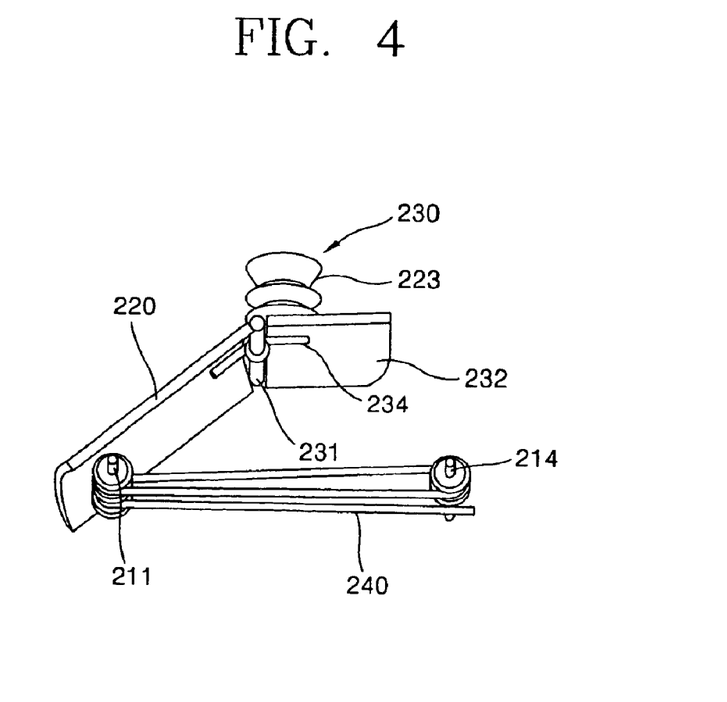
FIG. 4 is a perspective view showing a case where a suction unit is additionally installed on the wing of the micro capsule robot shown in FIG. 1.
Figure 5A:
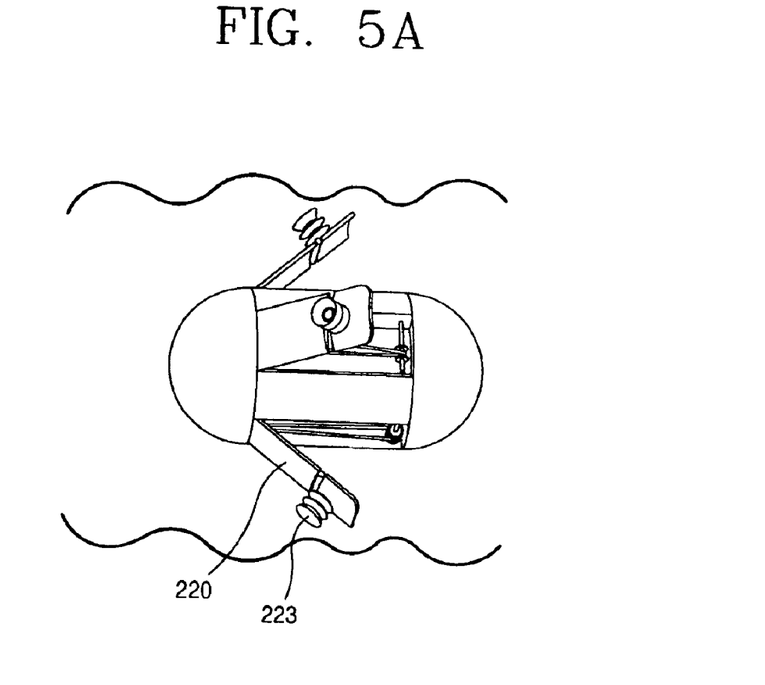
FIGS. 5a and 5b are perspective views showing operations of the micro capsule robot shown in FIG. 4 in the organ.
Figure 5B:
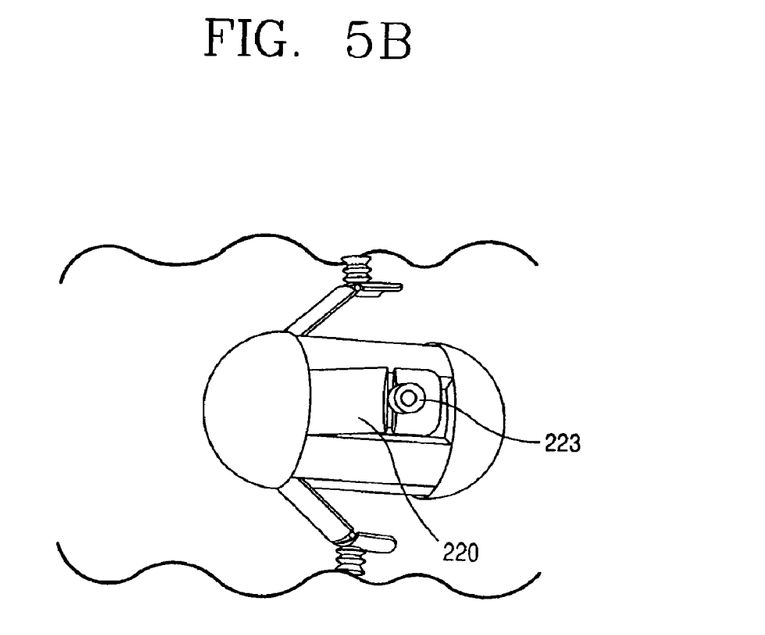

FIG. 1 is a perspective view showing the micro capsule robot according to the first embodiment of the present invention, FIG. 2 is a perspective view showing a status that wings of the micro capsule are unfolded, FIG. 3 is a perspective view showing driving principle of the wings on the micro capsule robot shown in FIG. 1, FIG. 4 is a perspective view showing a case that an suction unit is additionally installed on the wing of the micro capsule robot shown in FIG. 1, and FIGS. 5a and 5b are perspective views showing operations of the micro capsule robot shown in FIG. 4 in an organ.

As shown in FIGS. 1 through 4, the micro capsule robot according to the first embodiment of the present invention comprises: a body unit 100; a body movement control unit 200 including a linear driving device 210, and wings 220 which are unfolded from an outer circumferential surface of the body unit 100 by the operation of the linear driving device 210 to contact with an inner wall of an organ in order to control, i.e. to delay or stop a movement of the body unit 100, and installed on the outer circumferential surface of the body unit 100; and a controlling unit 420 installed in the body unit 100 for controlling the body movement control unit 200.

The body unit 100 comprises a body 101 of cylindrical shape, a front surface portion 102 and a rear surface portion 103 constructing a front surface and a rear surface of the body 101.

A camera device 111 and a lighting device 112 for examining inside of an organ are installed on the front surface portion 102, a loading space (S) is formed inside the body 101 to load a radio transmission/receive device 421 for transmitting/receiving with an outside apparatus 410, a controlling unit 420 and a power device (now shown).

Also, a sensor (not shown) which can recognize movements of the body unit 100 may be loaded in the loading space (S), and the sensor may be a force sensor, a speed sensor or a location sensor. The force sensor detects a contacted force when the wings 200 contact the inner wall of the organ, and the speed and location sensors detect information about moving speed or location of the robot.

Also, a plurality of concave recess portions 120 corresponding to the size of the wing 220 for receiving and fixing the body movement control unit 200 which will be described later are formed on the outer circumferential surface of the body unit 100 radially in a length direction of the body 101. The body movement control units 200 are respectively corresponded to the concave recess portions 120, and disposed in radial direction on the outer circumferential surface of the body unit 100.

The linear driving device 210 comprises: a first rotary shaft 211, which is fixedly installed on an end of the concave recess portion 120, having an end of the wing 220 fixedly installed thereon; a second rotary shaft 212 fixedly installed on the other end of the concave recess portion 120; and a linear driving member 240 wound on the first rotary shaft 211 and the second rotary shaft 212 in a state that one end is fixed on the first rotary shaft 211 and the other end is fixed on the body unit 100, and extended by a control signal of the controlling unit 420 to rotate the first rotary shaft 211 so as to unfold the wings 220.

A SMA (shape memory alloy) wire, Piezo or an EAP (electro active polymer) is used as the linear driving member 240. These are the driving members which are able to realize linear movement when electric current (or voltage) is applied.

A roller 214 or a pulley (not shown) for the linear driving member is installed on the first rotary shaft 211 and on the second rotary shaft 212. The linear movement according to the length changing of the linear driver 240 can be maximized through the roller 214.

Also, an elastic member 213 for returning the wings 220 to the body unit 100 is installed on the first rotary shaft 211. A torsion spring may be used as the elastic member 213. The torsion spring is mounted together with the roller 214.

As shown in FIG. 3, the wings 220 are formed to make a part of the outer circumferential surface of the body unit 100 by being fixedly installed on the first rotary shaft 211 and to be corresponded to the size of the concave recess portion 120 formed on the body unit 100 so as to move smoothly in the organ. For example, if the body unit 100 is formed as a cylinder, the outer circumferential surfaces of the wings 220 are formed as some parts of the cylinder.

Also, the wings 220 are unfolded from the outer circumferential surface of the body unit 100 according to the rotation of the first rotary shaft 211 by the driving of the linear driving device 210.

That is, the micro capsule robot according to the first embodiment of the present invention moves along with the organs of human body to photograph the inner walls of the organs and then, transmits the images out of the human body using the radio transmission/receive device 421. And the image information of the inner walls in the organs can be displayed by an image display device 411 such as a monitor.

Figure 6:
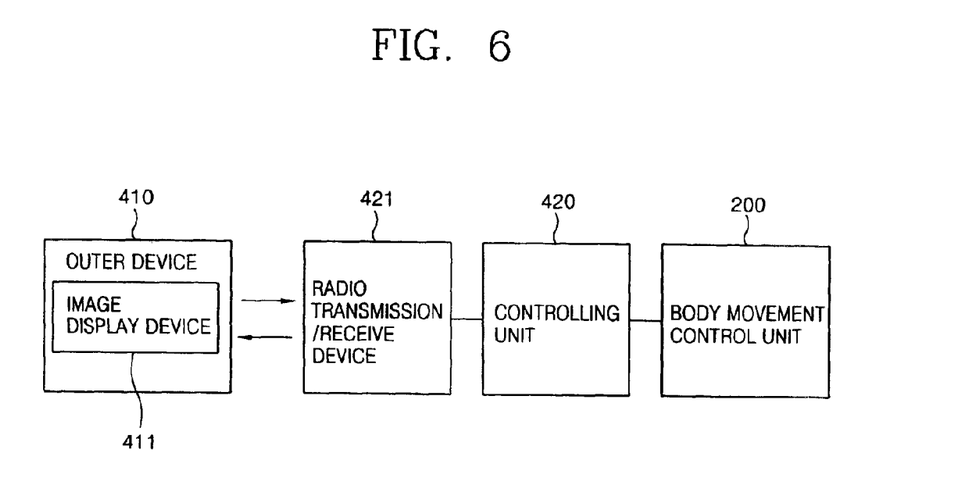
FIG. 6 is a block diagram for controlling the micro capsule robot according to the first embodiment of the present invention.

At that time, the observer controls the movement of the micro capsule robot by stopping or delaying in case that the micro capsule robot reaches to principal observation points in the organs. Then, as shown in FIG. 6, a control signal of stop or delay is transmitted through an outside apparatus, and the signal is transmitted to the controlling unit 420 through the radio transmission/receive device 421. Then, the controlling unit 420 controls body movement control unit 200 to unfold the wings 220 to stop or to delay the movement of the robot in the organs.

On the other hand, an suction portion 230 which can be attached on the inner wall of the organ may be additionally formed or installed on the end of the wing 220 so as to efficiently stop or to delay the movement of the micro capsule robot.

FIG. 4 is a perspective view showing a case that the suction portion is additionally installed on the wing of the micro capsule robot shown in FIG. 1, and FIGS. 5a and 5b are perspective views showing operations of the micro capsule robot of FIG. 4 in the organs.

As shown in FIG. 4, the suction portion 230 comprises a fixing axis 231 fixedly installed on the end of the wing 220, an auxiliary plate 232 rotatably coupled to the fixing axis 231, and a bellows 233 mounted on the auxiliary plate 232 and fixable on the inner wall of the organ. Also, the bellows 233 comprises a cup (not shown) for extending the contacted area, and a check valve (not shown) for forming vacuum pressure.

A recovery spring 234 for recovering the bellows 232 to the original status when the bellows 232 is separated from the inner wall of the organ is installed on the fixing axis 231.

As shown in FIGS. 5a and 5b, the cup of the suction portion 230 is contacted to the surface when the wings 220 close to the inner wall of the organ, and the vacuum is generated by the contraction of the bellows 233 and the suction force is generated. Therefore, the micro capsule is controls to be delayed or stopped on the inner wall of the organ.

On the other hand, the body movement control unit 200, especially the wings 220 can be constructed to proceed or to retrieve actively in the organ.

Figure 7:
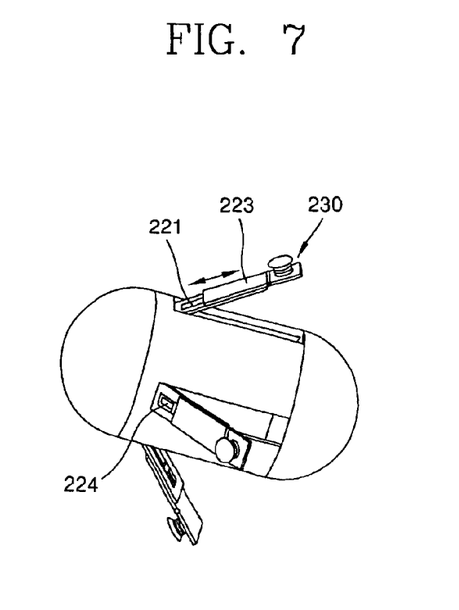
FIG. 7 is a perspective view showing a case that a body moving unit is additionally installed on the wing of the micro capsule robot shown in FIG. 4.
Figure 8:
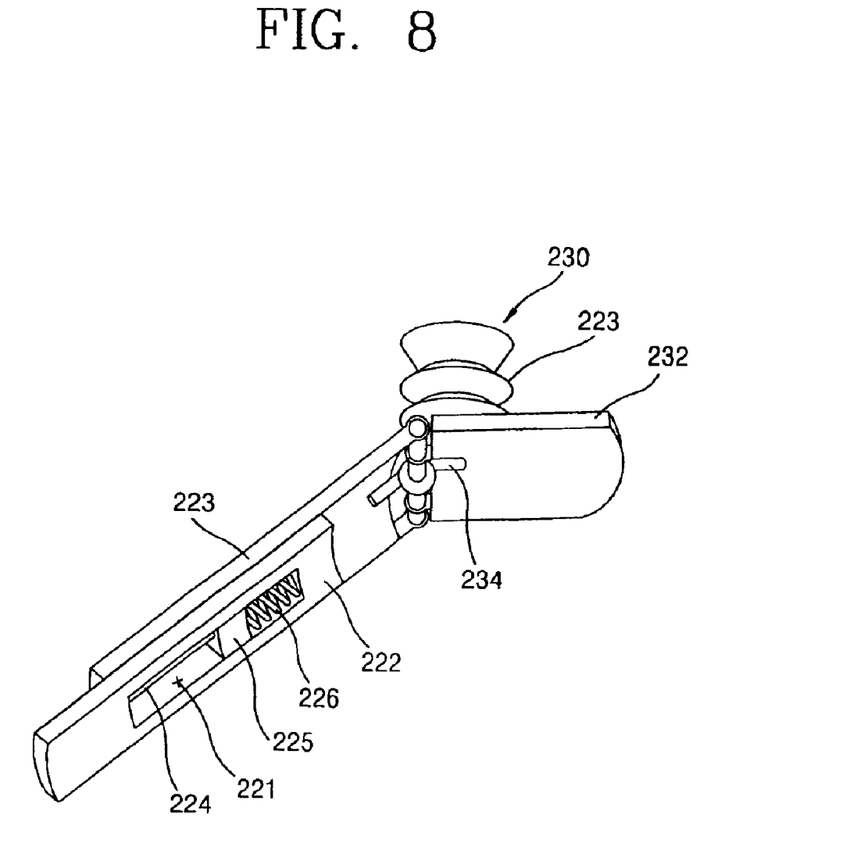
FIG. 8 is a perspective view showing a wing of the micro capsule robot shown in FIG. 7.

FIG. 7 is a perspective view showing a modified example of the wing on the micro capsule robot shown in FIG. 4, and FIG. 8 is a perspective view showing the wing of the micro capsule robot shown in FIG. 7.

That is, as shown in FIGS. 7 and 8, the wings 220 of the body movement control unit 200 make two or more pairs, and are disposed in radial direction on the outer circumferential surface of the body unit 100. And when a pair is fixed on the inner wall of the organ, the body unit 100 is moved in the organ by changing the length of the wings 220.

The wing 220 comprises a lower plate 222 on which a slot 221 is formed to change the length of the wing 220, an upper plate 223 coupled to the lower plate 222 so as to be slid along with the slot 221, and a linear driving device 224 connectedly installed between the upper and lower plates 223 and 222 on a fixing portion 225 which is fixedly installed on the upper plate 223 and extended by the control signal of the controlling unit 420 to make the upper plate 223 slid along with the slot 221. Also, an elastic member 226 is installed on an opposite part of the linear driver 224 to provide the upper plate 223 with the recovery force so that the upper plate 223 returns to the original position. Herein, as shown in FIG. 8, the suction portion 230 is rotatably coupled to the upper plate 223.

According to the above structure, when the length of each wing 220 is extended in a state that a pair of body movement control units 220 fixed on the inner wall of the organ, the body unit 100 proceeds. And when the process of fixing another pair of body movement control units 220 is repeated, the robot can be proceeded or retrieved.

Figure 9:
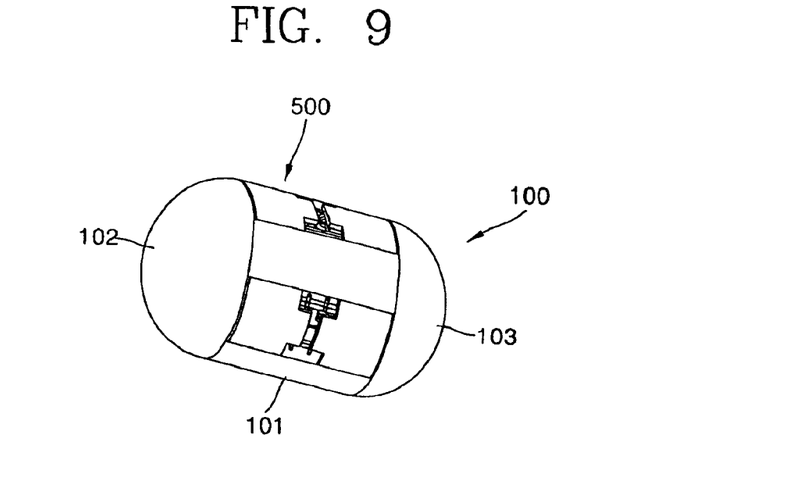
FIG. 9 is a perspective view showing a micro capsule robot according to the second embodiment of the present invention.
Figure 10:
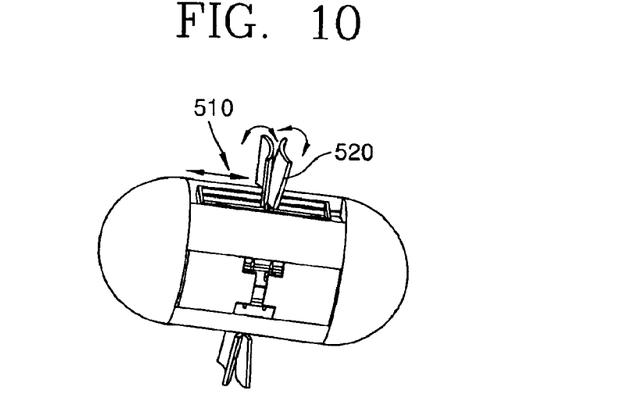
FIG. 10 is a perspective view showing a status that a wing of the micro capsule robot shown in FIG. 9 is unfolded.
Figure 11:
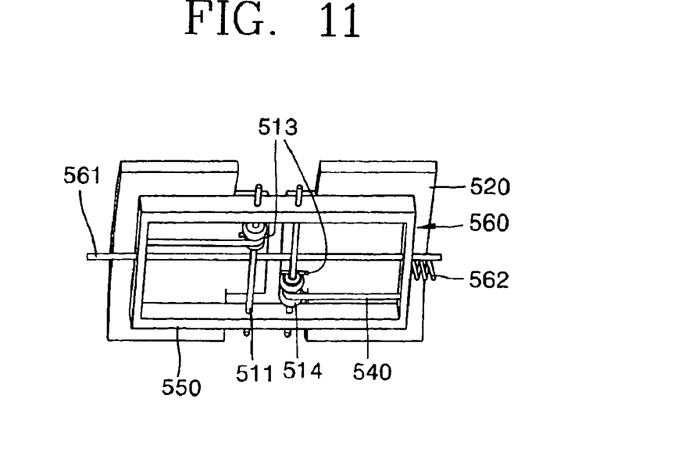
FIG. 11 is a perspective view showing a structure of a body movement control unit of the micro capsule robot shown in FIG. 9.
Figure 12A:
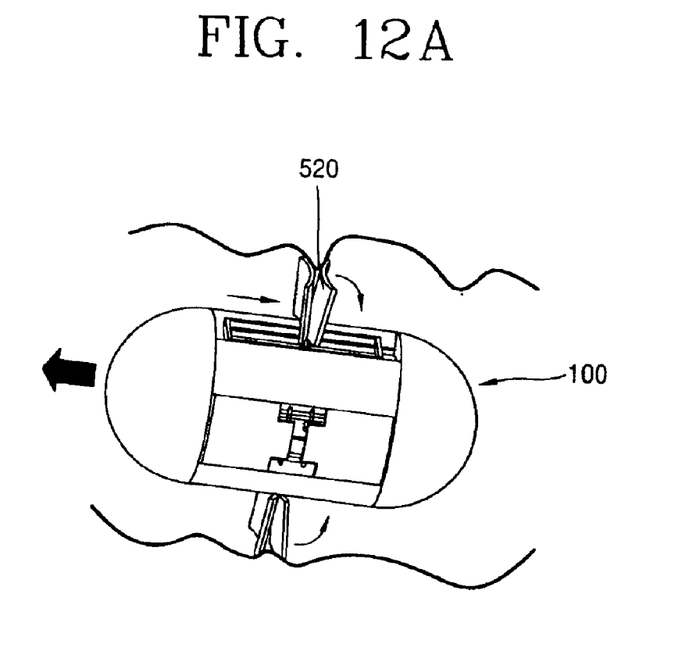
FIGS. 12A and 12B are perspective views showing operations of the micro capsule robot shown in FIG. 9 in an organ.
Figure 12B:
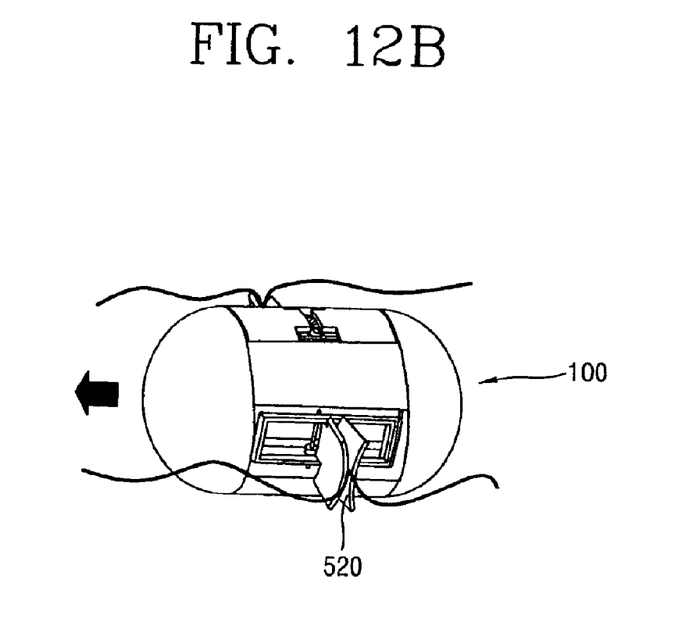

FIG. 9 is a perspective view showing a micro capsule robot according to the second embodiment of the present invention, FIG. 10 is a perspective view showing a status that wings of the micro capsule robot in FIG. 9 are unfolded, FIG. 11 is a perspective view showing a structure of a body movement control unit of the micro capsule robot shown in FIG. 9, and FIGS. 12A and 12B are perspective views showing operations of the micro capsule robot in FIG. 9 in the organs.

Meanwhile, the body movement control unit of the micro capsule robot according to the present invention can be constructed variously. That is, as shown in FIGS. 9 through 12A and 12B, a body movement control unit 500 of the micro capsule robot according to the second embodiment of the present invention includes a pair of wings 520 in a lengthy direction of the body unit 100.

In addition, a linear driving device 510 comprises a fixing frame 550 fixedly installed on the outer circumferential surface of the body unit 100, a first rotary shaft 511, on which a pair of wings 520 are fixedly installed, installed on a center of the fixing frame 550, and a pair of linear drivers 540 wound on the first rotary shaft 511 in a state that one end is fixedly installed on the first rotary shaft 511 and the other end is fixedly installed on the fixing frame 550, and extended according to the control signal of the controlling unit 420 so as to unfold the wings 520 in order to rotate the first rotary shaft 511.

The fixing frame 550 may be installed integrally with the body unit 100, however, may be installed by forming an additional concave recess portion 120 in a lengthy direction of the outer circumferential surface of the body unit 100 so that the fixing frame 550 can be received therein.

An elastic member, that is, a recovery spring may be additionally installed on the first rotary shaft 511 to provide the wings 520 with the recovery force as in the first embodiment of the present invention.

In addition, rollers 514 for the linear driver 540 are installed on the first rotary shaft 511.

As shown in FIG. 9, in the micro capsule robot according to the second embodiment of the present invention having the above structure, the pair of wings 520 makes the same surface with the outer circumferential surface of the body unit 100, and does not affect to the movement of the robot.

On the contrary, in case that the movement of the robot should be controlled to be delayed or stopped, a signal is transmitted to the controlling unit 420, and the controlling unit 420 operates the linear driver 540 to control to delay or to stop the moving of the robot on the inner wall of the organ as shown in FIGS. 10 and 12.

Meanwhile, the micro capsule robot according to the second embodiment of the present invention should move by itself on the inner wall of the organ, and therefore, a body moving unit which can move by itself in the organ can be additionally installed on the micro capsule robot according to the present invention.

That is, as shown in FIG. 11, the body moving unit 560 is additionally installed on the body unit 100 in order to move the body unit 100 by making the fixing frame 550 linearly move when the body movement control unit 500 is fixed on the inner wall of the organ.

The body moving unit 560 comprises the concave recess portion 120 formed on the outer circumferential surface of the body unit 100 for receiving the fixing frame 550 so as to linearly move, a linear driver 561 installed on an end of the fixing frame 550 and extended according to the control signal of the controlling unit 420 to move the fixing frame 550 toward the lengthy direction of the body unit 100, and an elastic member 562 installed on the other end of the fixing frame and on the concave recess portion 120 for returning the fixing frame 550 to the original position.

As shown in FIGS. 12A and 12B, the body moving unit 560 moves the fixing frame 550 in the concave recess portion 120 to proceed or retrieve the robot in the state that the body movement control unit 500 fixes the body on the inner wall of the organ.

Especially, when the number of the body movement control units 500 is constructed to be plural, for example, two body movement control units 500 are constructed, the body movement control unit 500 is fixed on the inner wall of the organ and the body unit 100 is proceeded or retrieved by moving the fixing frame 550. Then, another body movement control unit 500 is fixed on the inner wall of the organ, the body movement control unit 500 which was fixed on the wall before is released, and the above processes are repeated sequentially, then, the micro capsule robot can move more effectively.

Figure 13:
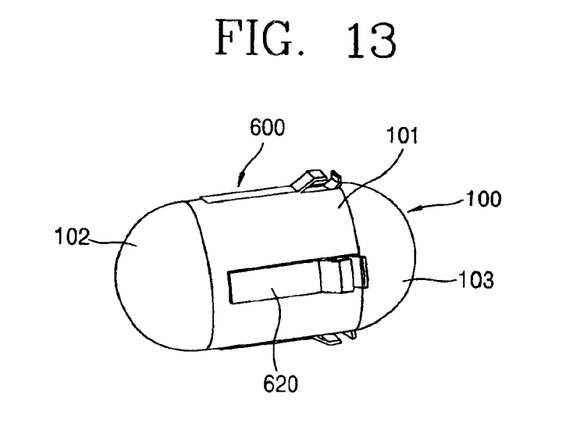
FIG. 13 is a perspective view showing a micro capsule robot according to a third embodiment of the present invention.
Figure 14:
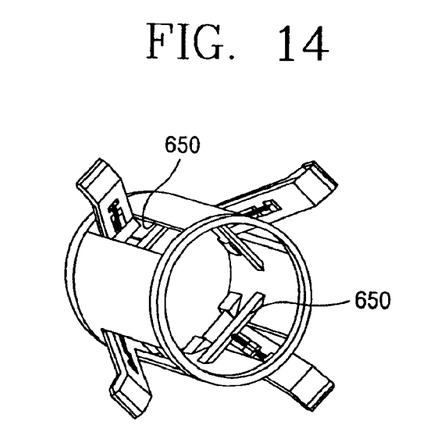
FIG. 14 is a partial perspective view showing a part of the micro capsule robot shown in FIG. 13.
Figure 15:
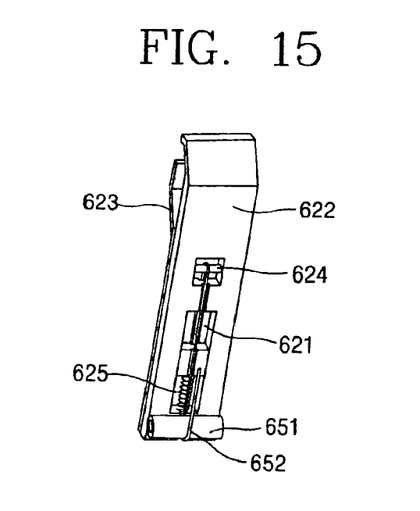
FIG. 15 is a perspective view showing a part of the micro capsule robot shown in FIG. 13.
Figure 16:
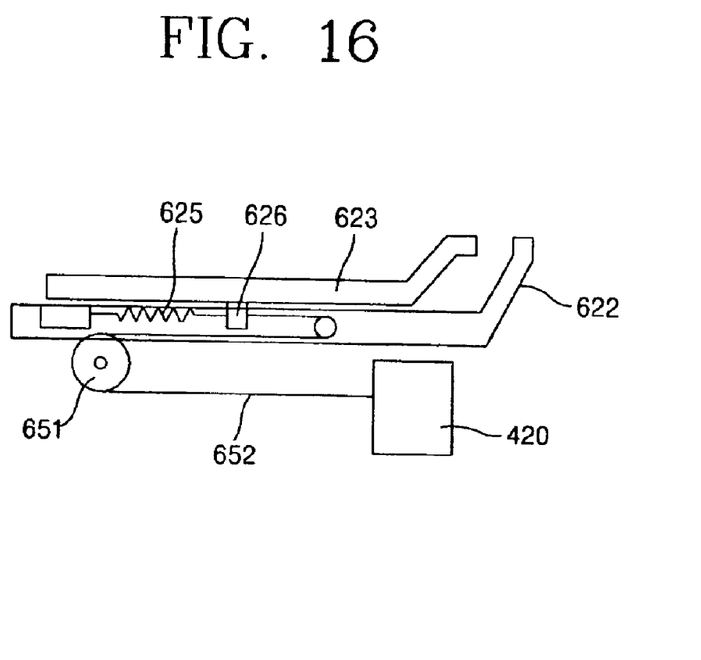
FIGS. 16 and 17 are perspective views showing operations of the body movement control unit of the micro capsule robot shown in FIG. 13.
Figure 17:
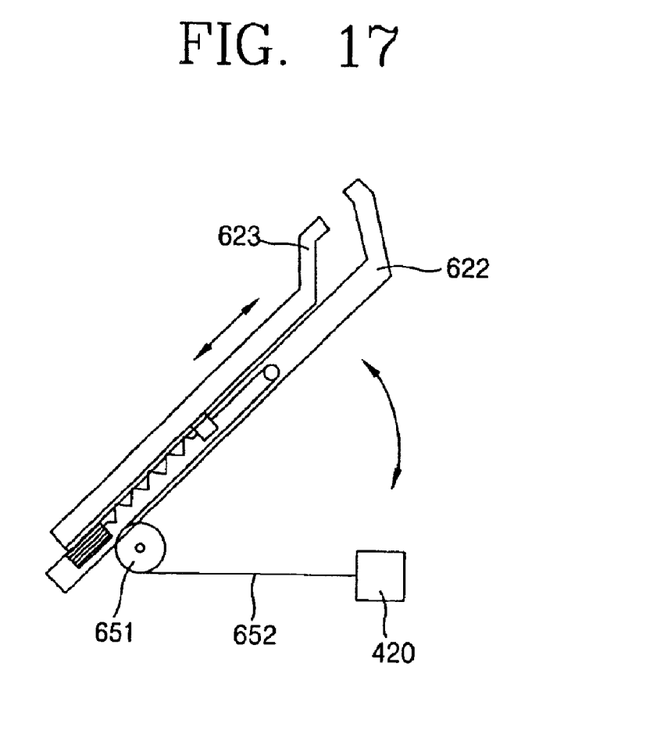

FIG. 13 is a perspective view showing a micro capsule robot according to a third embodiment of the present invention, FIG. 14 is a partial perspective view showing a part of the micro capsule robot of FIG. 13, and FIG. 15 is a perspective view showing wings of the micro capsule robot shown in FIG. 13, and FIGS. 16 and 17 are perspective views showing operations of a body movement control unit of the micro capsule robot shown in FIG. 13.

The micro capsule robot according to the third embodiment of the present invention is a modified embodiment of the body movement control unit in the micro capsule robot shown according to the first embodiment of the present invention.

That is, as shown in FIGS. 13 through 15, a wing 620 of the body movement control unit 600 comprises a lower plate 622 on which a slot 621 is formed, an upper plate 623 coupled to the lower plate 622 so as to be slid along with the slot 621 and forming nippers with a free end of the lower plate 622, a supporting axis 624 installed on the lower plate 622 with a certain distance from the fixed end as passing through the slot 621, and an elastic member 625 connected to a fixing portion 626 which is inserted into the slot 621 of the upper and lower plates 623 and 622 so as to recover the upper plate 623 to the original position.

The linear driving device 640 comprises a fixing frame 650 fixedly installed on the outer circumferential surface of the body unit 100, a rotary shaft 651, on which the fixed end of the lower plate 622 is fixedly installed, fixedly installed on the fixing frame 650, and a linear driver 652 having one end fixed on the lower plate 622 and the other end fixed on the fixing frame 650 as passing through the supporting axis 624 and the rotary shaft 651, and extended by the control signal of the controlling unit 420 for rotating the rotary shaft 651 so as to unfold the wings 620.

As shown in FIG. 13, in the micro capsule robot according to the third embodiment of the present invention, the wings 620 make a same surface with the outer circumferential surface of the body unit 100 when the robot moves in the organ, and the controlling unit 420 operates the linear driver 652 according to a delay or stop signal of the outside apparatus, and the wings 620 are unfolded as the linear driver 652 is operated.

As the wings 620 are unfolded, the wings 620 are contacted to the inner wall of the organ, and the linear driver 652 pulls the upper plate 623 of the wings 620 to catch the inner wall of the organ, and thereby, the body unit 100 is fixed on the inner wall. The above driving principles are shown in FIGS. 16 and 17.

The micro capsule robot according to the present invention provides a means which is able to control to delay or stop the movement of the robot during moving the robot in an organ of human body, and therefore, the inner status of the organ can be examined more effectively.

Also, the micro capsule robot according to the present invention provides a moving and delaying means which is modulated, and therefore, the fabrication and assembly of the present invention can be made easily.

Also, the micro capsule robot according to the present invention provides a moving means, and thereby, the robot is able to move actively in the organ.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A micro capsule robot comprising:
a body unit;
a body movement control unit, which is installed on an outer circumferential surface of the body unit, including a linear driving device, and wings which are unfolded from the outer circumferential surface of the body unit by operation of the linear driving device for controlling a movement of the body unit; and
a controlling unit installed in the body unit for controlling the body movement control unit, and
wherein the linear driving device comprises:
a fixing frame fixedly installed on the outer circumferential surface of the body unit;
a rotary shaft, on which one end of the wine is fixedly installed, fixedly installed on one end of the fixing frame; and
a linear driver wound on the rotary shaft in a state that one end is fixed on the rotary shaft and the other end is fixed on the fixing frame, and extended by a control signal of the controlling unit to rotate the rotary shaft so as to unfold the wings.

2. The robot of claim 1, wherein the body unit includes a loading space for loading inner devices formed on center portion thereof.

3. The robot of claim 2, wherein a camera device, a lighting device and a sensor for recognizing movements of the body unit are installed on the loading space.

4. The robot of claim 1, wherein an elastic member for returning the wings to the body unit from the unfolded state is additionally installed on the rotary shaft.

5. The robot of claim 1, wherein the body unit includes a concave recess portion formed on the outer circumferential surface of the body unit in a lengthy direction of the body unit so as to be corresponded to the wings for receiving and fixing the body movement control unit.

6. The robot of claim 5, wherein the concave recess portion and the fixing frame are formed as integrally with each other.

7. The robot of claim 1, wherein a second rotary shaft is additionally installed on the other end of the fixing frame, and the linear driver is wound on the second rotary shaft.

8. The robot of claim 1, wherein suction portions which are fixed on inner wall of an organ when these are contacted to the inner wall of the organ are additionally installed on an end of the wings.

9. The robot of claim 8, wherein the suction portion includes a fixing axis fixedly installed on the end of the wing, an auxiliary plate rotatably coupled to the fixing axis, and a bellows mounted on the auxiliary plate and fixedly adsorbed on the inner wall of the organ.

10. The robot of claim 9, wherein a recovery spring for returning the bellows to the original status when the bellows is separated from the inner wall of the organ is additionally installed on the fixing axis.

11. The robot of claim 1, wherein the number of the body movement control unit is constructed to be plural and disposed on the outer circumferential surface of the body unit in a radial direction of the body unit.

12. The robot of claim 1, wherein a length of the wing is changed according to the control signal of the controlling unit.

13. A micro capsule robot comprising:
a body unit;
a body movement control unit, which is installed on an outer circumferential surface of the body unit, including a linear driving device, and wings which are unfolded from the outer circumferential surface of the body unit by operation of the linear driving device for controlling a movement of the body unit; and
a controlling unit installed in the body unit for controlling the body movement control unit,
wherein the wing comprises:
a lower plate on which a slot is formed;
an upper plate coupled to the lower plate to be slid along with the slot; and
a sliding linear driver connected between the upper and lower plates and extended by the control signal of the controlling unit for making the upper plate slide along with the slot.

14. The robot of claim 13, wherein the body movement control unit is constructed to be two or more pairs, and moves in the organ by changing the length of the wing when a pair of body movement control units are fixed on the inner wall of the organ.

15. A micro capsule robot comprising:
a body unit;
a body movement control unit, which is installed on an outer circumferential surface of the body unit, including a linear driving device, and wines which are unfolded from the outer circumferential surface of the body unit by operation of the linear driving device for controlling a movement of the body unit; and a controlling unit installed in the body unit for controlling the body movement control unit, wherein the linear driving device comprises:

a fixing frame fixedly installed on the outer circumferential surface of the body unit; a first rotary shaft, on which the pair of wings is fixedly installed, installed on a center of the fixing frame;

a pair of second rotary shafts installed on both ends of the fixing frame; and a pair of linear drivers wound on the first and second rotary shafts in the state that one ends are fixedly installed on the first rotary shaft and the other ends are fixedly installed on the fixing frame, and extended by the control signal of the controlling unit for rotating the first rotary shaft so as to unfold the wings.

16. The robot of claim 15, wherein a body moving unit for moving the body unit by making the fixing frame linearly move when the body movement control unit is fixed on the inner wall of the organ is additionally installed on the body unit.

17. The robot of claim 16, wherein the body moving unit comprises:

a concave recess portion formed on the outer circumferential surface of the body unit for receiving the fixing frame so that the fixing frame can be linearly moved;

a linear driver installed on one end of the fixing frame and extended by the control signal of the controlling unit for moving the fixing frame to the lengthy direction of the body unit; and an elastic member installed on the other end of the fixing frame and on the concave recess portion for returning the fixing frame to the original position.

18. A micro capsule robot comprising:

a body unit;

a body movement control unit, which is installed on an outer circumferential surface of the body unit, including a linear driving device, and wings which are unfolded from the outer circumferential surface of the body unit by operation of the linear driving device for controlling a movement of the body unit; and a controlling unit installed in the body unit for controlling the body movement control unit, wherein the wing comprises:

a lower plate on which a slot is formed;

an upper plate coupled to the lower plate so as to be slid along with the slot and forming nippers with a free end of the lower end;

a supporting shaft installed on the lower plate with a certain distance from the fixed end as passing through the slot; and an elastic member connected between the upper and lower plates so that the upper plate can be recovered to the original position, and the linear driving device comprises:

a fixing frame fixedly installed on the outer circumferential surface of the body unit; a rotary shaft, on which the fixed end of the lower plate is fixedly installed, fixedly installed on the fixing frame; and a linear driver having one end fixed on the lower plate and the other end fixed on the fixing frame as passing through the supporting shaft and the rotary shaft, and extended by the control signal of the controlling unit for rotating the rotary shaft so as to unfold the wings.

19. The robot of claim 1, wherein the linear driver is a shape memory alloy wire, a piezo or an electro active polymer.

* * * * *